United States Patent
Tochikubo et al.

[19]

[11] Patent Number: 6,106,478
[45] Date of Patent: Aug. 22, 2000

[54] SPHYGMOMANOMETER UTILIZING OPTICALLY DETECTED ARTERIAL PULSATION DISPLACEMENT

[75] Inventors: Osamu Tochikubo, Kanagawa; Shigehiro Ishizuka, Saitama, both of Japan

[73] Assignee: A & D Company, Limited, Tokyo, Japan

[21] Appl. No.: 08/983,144

[22] PCT Filed: Jun. 25, 1996

[86] PCT No.: PCT/JP96/01750

§ 371 Date: Jan. 13, 1999

§ 102(e) Date: Jan. 13, 1999

[87] PCT Pub. No.: WO97/49331

PCT Pub. Date: Dec. 31, 1997

[51] Int. Cl.[7] ..................................................... A61B 5/02
[52] U.S. Cl. ........................... 600/494; 600/490; 600/493
[58] Field of Search .................................. 600/481, 490, 600/493, 494, 495, 496, 499, 500, 501, 502, 310, 473, 477

[56] References Cited

U.S. PATENT DOCUMENTS

| | | | |
|---|---|---|---|
| 3,633,567 | 1/1972 | Sarnoff | 600/499 |
| 4,170,226 | 10/1979 | Alabainy et al. | 600/480 |
| 4,653,506 | 3/1987 | Romanovskaya | 600/490 |
| 4,771,790 | 9/1988 | Yamasawa et al. | 600/480 |
| 4,850,369 | 7/1989 | Yamasawa et al. | 600/480 |
| 4,860,761 | 8/1989 | Yamasawa et al. | 600/480 |
| 4,862,895 | 9/1989 | Yamasawa et al. | 600/480 |
| 4,869,261 | 9/1989 | Penaz | 600/480 |
| 5,172,696 | 12/1992 | Souma | 600/473 |
| 5,222,020 | 6/1993 | Takeda | 600/490 |
| 5,425,372 | 6/1995 | Takeda | 600/490 |
| 5,626,141 | 5/1997 | Takeda | 600/490 |
| 5,840,037 | 11/1998 | Tochikubo et al. | 600/499 |

FOREIGN PATENT DOCUMENTS

| | | |
|---|---|---|
| 60-60833 | 4/1985 | Japan . |
| 2-31734 | 2/1990 | Japan . |
| 5-35104 | 5/1993 | Japan . |
| 5-329113 | 12/1993 | Japan . |

OTHER PUBLICATIONS

International Search Report.

*Primary Examiner*—Cary O'Connor
*Assistant Examiner*—Navin Natnithithadha
*Attorney, Agent, or Firm*—Nixon Peabody LLP; Thomas W. Cole

[57] ABSTRACT

The invention relates to a sphygmomanometer capable of highly accurately judging the maximum blood pressure and minimum blood pressure, which has a cuff 10 which is attached to an appointed portion of a patient and presses the artery by supplying air therein; an optical range sensor 12 which is located opposite said cuff 10 and is able to detect the pulsation displacement of said artery; a digital processing section 14 which is able to judge the maximum and minimum blood pressure of said patient on the basis of photoelectric volumetric pulse wave signals sent out by said optical range sensor 12; and a display section 38 which is able to display the maximum and minimum blood pressure values judged by said digital data processing section 14. When increasing the pressure of the cuff 10 at a constant speed, said digital data processing section 14 is able to judge as the maximum blood pressure the point of disappearance of a photoelectric volumetric pulse wave signal and to judge as the minimum blood pressure the point of appearance of a flat section on the photoelectric volumetric pulse wave signal or its vicinity.

4 Claims, 7 Drawing Sheets

SPHYGMOMANOMETER UTILIZING OPTICALLY DETECTED ARTERIAL PULSATION DISPLACEMENT

BACKGROUND OF THE INVENTION

1. Field of the Invention

The present invention relates to a sphygmomanometer, and in particular relates to a closed type sphygmomanometer.

2. Description of the Related Art

A closed type electronic sphygmomanometer in which a cuff pressing the artery is wound on the upper arm of a patient is already known. For a tonometry hemadynamometry method with this kind of sphygmomanometer, although there are an oscillometric process, a Korotoff's sound method, an impedance method, etc., the oscillometric process has been mainly utilized in clinical applications. A sphygmomanometer in which a tonometry hemadynamometry method utilizing such an oscillometric process is employed is disclosed by, for example, Japanese patent Publication No. 28637 of 1994.

A sphygmomanometer disclosed in the above publication is basically composed of a cuff which is attached to the upper arm of a patient and presses the artery by supplying air therein, a measuring section which is able to detect the superposed pressure of the drop pressure and pulse pressure which change in said cuff and convert the same into digital signals, a digital data processing section which is able to obtain the maximum and minimum blood pressure values of a patient by using the cuff pressure detection signals outputted by said measuring section as input data, and a display section which is able to display the maximum and minimum blood pressure values calculated by said digital data processing section.

With a sphygmomanometer constructed as described above, the maximum and minimum blood pressure values are judged by the digital data processing section on the basis of fluctuations of the pulse pressure vibrations and pulse wave amplitude while causing the pressure in the cuff to drop at a constant rate. However, there were the following shortcomings in this tonometry hemadynamometry method with such an oscillometric process.

That is, in the tonometry hemadynamometry method, as has been represented by an in-artery catheter method, the method for measuring the pressure applied to a blood vessel wall by determining one point of the artery of a patient is ideal. However, with the tonometry hemadynamometry method by the abovementioned oscillometric method, since the pressure fluctuations in the cuff wound on the upper arm of a patient is detected and is used for measuring the blood pressure, a pulse pressure appears even in the in-cuff pressure which is higher than the maximum blood pressure or it is not clear to judge the minimum blood pressure.

With the tonometry hemadynamometry method with a conventional oscillometric process, this results from detecting the mean pulsation of the artery spreading in the range of the cuff, and the pulsation is such that the artery wall displacement of the brachial artery resulting from the heartbeat is propagated as displacements of the skin surface and further the displacement of the skin surface causes the air capacity in the cuff to be changed, wherein this capacity change is detected as a pressure change in the cuff. Resultantly, the displacement quantity of the artery wall is converted to the pressure fluctuation in the cuff.

However, with such a method, since the displacement quantity of the artery wall is measured via air in the cuff, it is not possible to faithfully obtain the artery wall displacement with only the pulse pressure wave obtained from inside the cuff because of receiving influences outside the body such as compression characteristics of air, damping characteristics thereof, etc.

This also means that although constituents of Korotoff's sounds which have higher frequency constituents than the pulse pressure waves are superposed with the pulse waveforms in a cuff pressure dropping process from the maximum blood pressure to the minimum blood pressure in the blood pressure measurement and must appear, fluctuations of higher frequency constituents such as Korotoff's sounds are not able to be propagated since air is used as a propagation medium in the in-cuff pulse pressure waveform in the oscillometric process, and resultantly it seems that such constituents do not appear.

That is, in a tonometry hemadynamometry method with a conventional oscillometric process, since a cuff is wound onto a long length of the brachial artery which is the portion to be measured of a patient and the pulse pressure vibrations are detected as pressure fluctuations in the cuff pressure, the artery pressure of the artery wall at one point which is ideal in the tonometry hemadynamometry method is not accurately reflected. Accordingly, a pulse pressure wave occurs in the cuff pressure which is more than the maximum blood pressure, and since the pulse pressure wave is propagated by using air as a medium, the frequency propagation is adversely influenced by the compression characteristics and damping characteristics of air, and a shortcoming is caused, whereby Korotoff's sound propagation is hindered.

SUMMARY OF THE INVENTION

The present invention was developed in view of solving these shortcomings, and it is therefore an object of the invention to provide a sphygmomanometer which is able to accurately measure the blood pressure by directly measuring a local artery wall displacement. Disclosure of the invention In order to solve the object, the invention is characterized in having a cuff which is attached to an appointed portion of a patient and presses the artery by supplying air therein, an optical range sensor which is located opposite said cuff and is able to detect the pulsation displacement of said artery, a digital processing section which is able to judge the maximum and minimum blood pressure of said patient on the basis of photoelectric volumetric pulse wave signals sent out by said optical range sensor, and a display section which is able to display the maximum and minimum blood pressure values judged by said digital data processing section.

Said optical range sensor may be composed of a reflection plate provided inside an air bag of said cuff and light receiving and light emitting diodes which are provided outside said air bag.

Furthermore, said optical range sensor has a pair of light receiving and light emitting diodes, one of which may be provided inside said air bag of the cuff and the other of which may be provided outside the air bag thereof.

Said digital data processing section is able to judge as the maximum blood pressure the point of disappearance or appearance of said photoelectric volumetric pulse wave signals when raising or lowering the pressure in said cuff at a constant speed, and is able to judge as the minimum blood pressure the point of radical reduction of said photoelectric volumetric pulse wave signals or its vicinity.

When raising or lowering the pressure in the cuff at a constant speed, the digital data processing section is able to judge as the maximum blood pressure the point of appearance or disappearance of said photoelectric volumetric pulse wave signals and is able to judge as the minimum blood pressure the point of Korotoff's sound constituents from said photoelectric volumetric pulse wave signals or its vicinity.

Furthermore, when raising or lowering the pressure in the cuff at a constant speed, the digital data processing section is able to judge as the maximum blood pressure the point of appearance or disappearance of said photoelectric volumetric pulse wave signals and is able to judge as the minimum blood pressure the point of appearance of a flat section in said photoelectric volumetric pulse wave signals or its vicinity.

A sphygmomanometer constructed as described above has an optical range sensor which is secured opposite the cuff and is able to detect the pulsation displacement of said artery. On the basis of photoelectric volumetric pulse wave signals outputted from said optical range sensor, since the digital data processing section judges the maximum blood pressure and minimum blood pressure of a patient, the displacement quantity of a local artery wall is able to be directly measured, and it is possible to obtain the maximum blood pressure value and minimum blood pressure value on the basis of this displacement quantity.

DETAILED DESCRIPTION OF THE INVENTION

Figure 1:
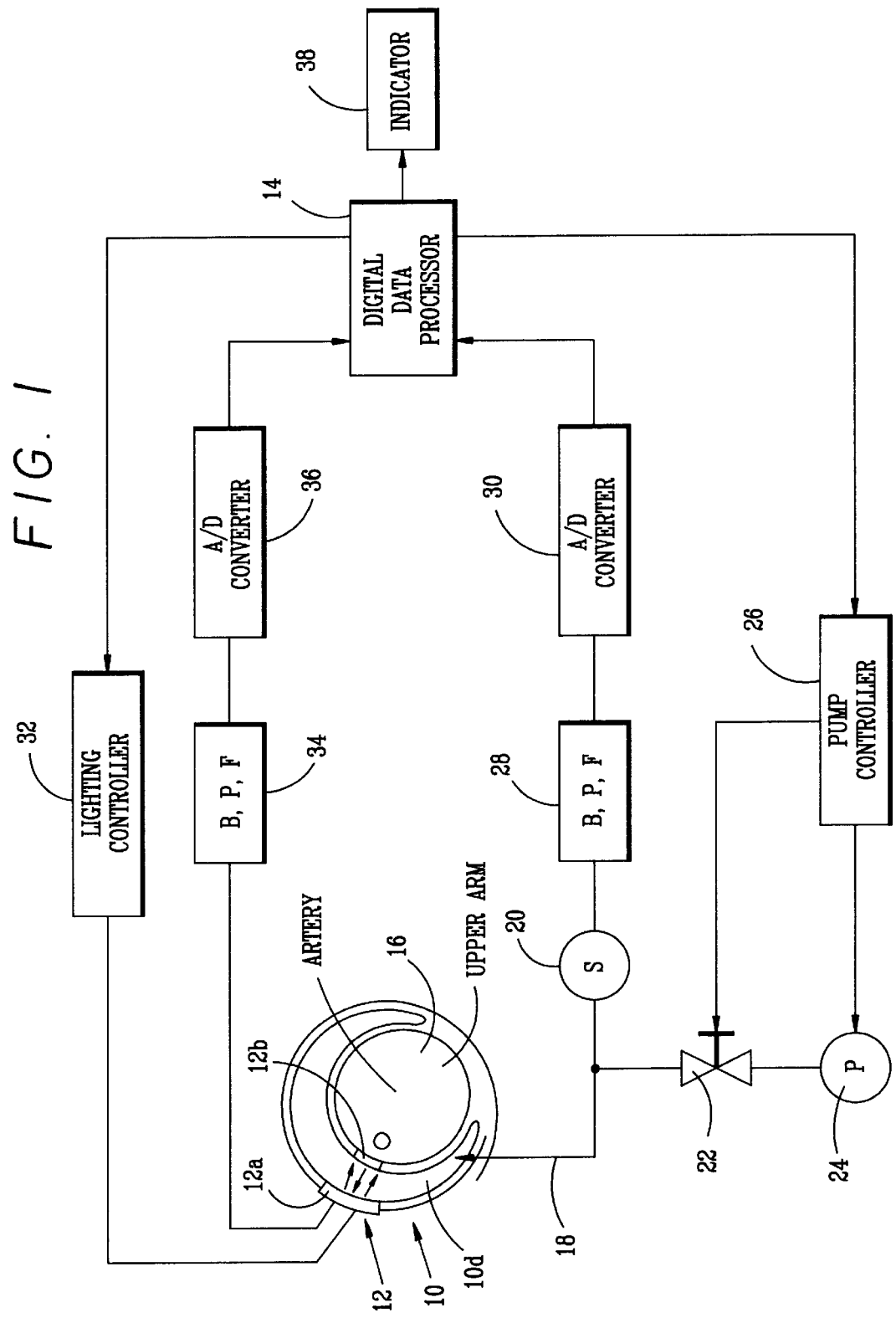
FIG. 1 is a block diagram of the total construction showing a preferred embodiment of a sphygmomanometer according to the invention.
Figure 2A:
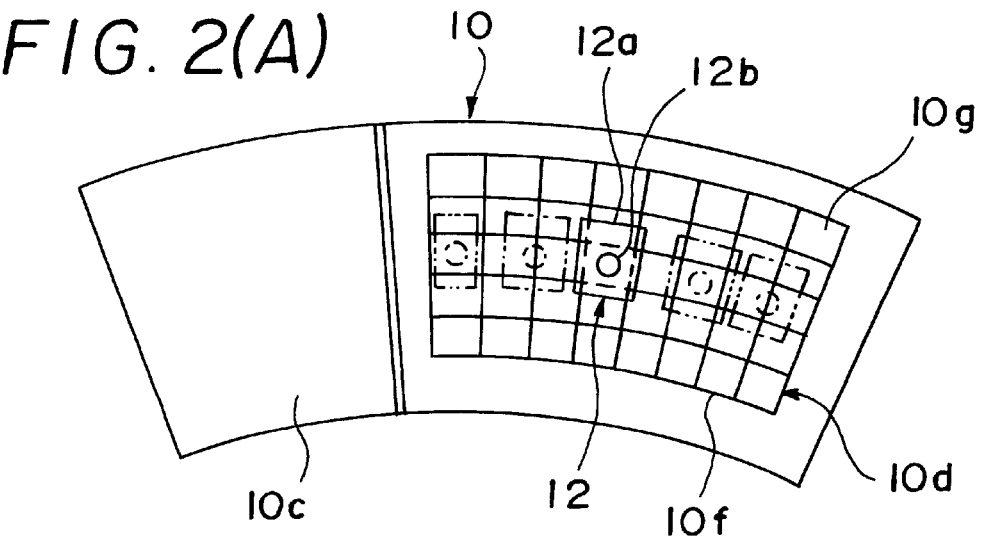
FIG. 2 is a developed view of a cuff for a sphygmomanometer of FIG. 1 and a cross-sectional view of major parts thereof.
Figure 2B:
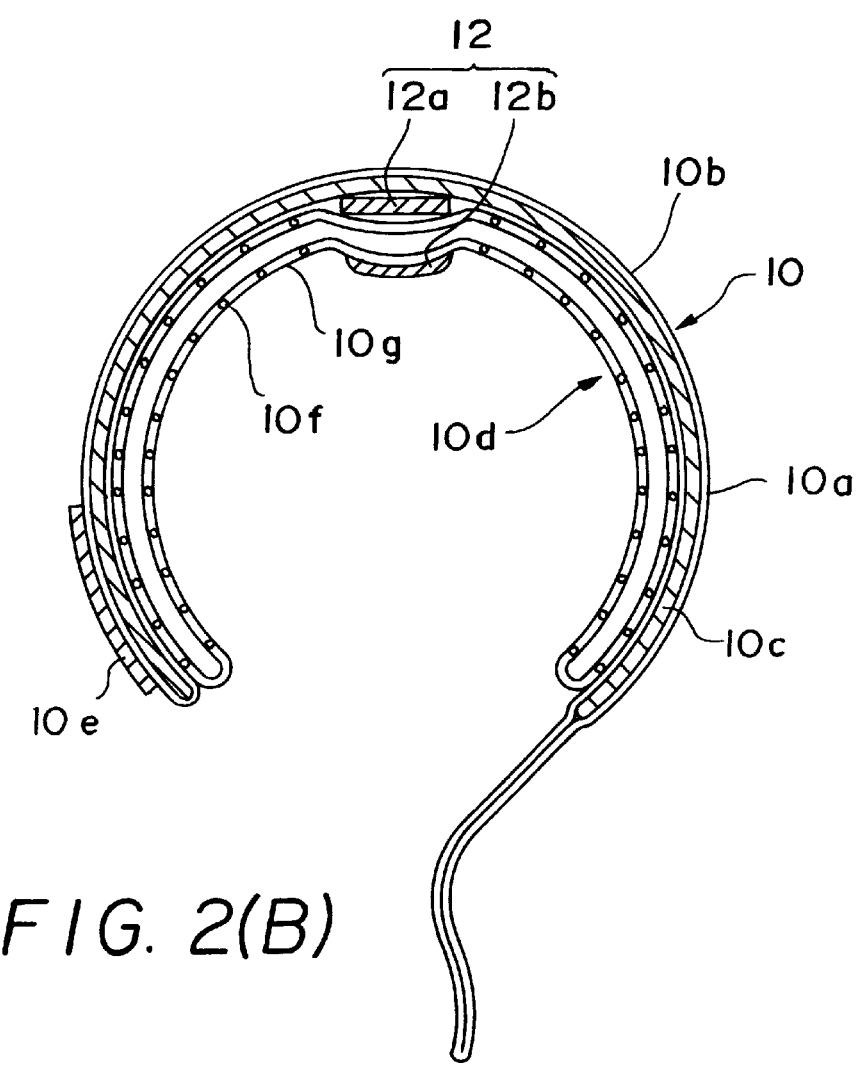

Preferred embodiments of the invention are described with reference to the accompanying drawings. FIG. 1 through FIG. 4 show a preferred embodiment of a sphygmomanometer according to the invention. A sphygmomanometer shown in these drawings has a cuff 10, an optical range sensor 12, and a digital data processing section 14. Said cuff 10 is applied to an appointed part of a patient, and concretely is applied to the upper arm 16, the detail of which is shown in FIG. 2.

Said cuff 10 shown in the drawing is made of thin synthetic resin and is formed to be arcuate. Said cuff 10 consists of a bendable and deformable hard curved plate 10a, an outer cloth 10b which surrounds the outer circumference of said curved plate 10a, an inner cloth 10c sewed to said outer cloth 10a so that the same is able to surround the inner circumference of said curved plate 10a, an air bag 10d provided inside the inner cloth 10c, and an engaging fastener 1e sewed to the outer circumference of said outer cloth 10b, which is engageable with the end portion of the inner cloth 10c.

Said air bag 10d is a transparent sealed bag member 10g made of synthetic resin sheet, which has reinforcing fibers 10f incorporated therein in a latticed state. Said reinforcing fibers 10f are integrally incorporated so as to prevent the same from being elongated when compressing air therein and the artery is in pulsation. When air is supplied into the bag member 10g via a tube 18 described later and said air bag is inflated therewith, the bag member 10g is able to be inflated in proportion to the supply quantity of air.

An air supplying tube 18 is caused to communicate with and is connected with the inside of the bag member 10g. A pressure sensor 20 and a solenoid control valve 22 are connected to the outer end of said tube 18. And a pump 24 which sends out air is connected to the solenoid control valve 22, whereby the solenoid control valve 22 and pump 24 are controlled by a pump control section 26.

Detection signals of the pressure sensor 20 are inputted into the digital data processing section 14 via a band pass filter 28 and an A/D converter 30. Control signals are sent out from the digital data processing section 14 to the pump control section 26 on the basis of the detection signals of the pressure sensor 20. The optical range sensor 12 is composed of a photocoupler 12a fixed at the outer surface of the outer section of the bag member 10g and a reflection plate 12b fixed on the outer surface of the inner section of the bag member 10g so that the same is opposite this photocoupler 12a.

The photocoupler 12a is such that a light emitting diode and a phototransistor are integrally combined with each other, and the same is set so that light emitted from the light emitting diode is reflected by the reflection plate 12b and is made incident into the phototransistor. The output level of the phototransistor may differ according to the distance between the photocoupler 12a and the reflection plate 12b, whereby output signals corresponding to the displacement of the artery are sent out.

The light emitting diode of the photocoupler 12a is controlled to be turned on and off by a light emission control section 32 connected to the digital data processing section 14. The digital data processing section 14 is connected to the phototransistor of the photocoupler 12a via the band pass filter 34 and A/D converter 36, whereby the detection signals of the phototransistor are digitalized and inputted into the processing section 14.

Furthermore, with this preferred embodiment, since the bag member 10g is formed with a transparent synthetic resin sheet, the photocoupler 12a and reflection plate 12b are disposed at the outside thereof. However, in a case where the bag member 10g is formed with a non-transparent synthetic resin sheet, the photocoupler 12a and reflection plate 12b are disposed at the inside thereof.

With a sphygmomanometer according to the invention, the optional range sensor 12 may be not only a combination of a photocoupler 12a and a reflection plate 12b but also a combination of a light emitting diode and a photocoupler. In this case, they may be disposed so that they are opposite the inside or outside of the bag member 10g.

Figure 3:
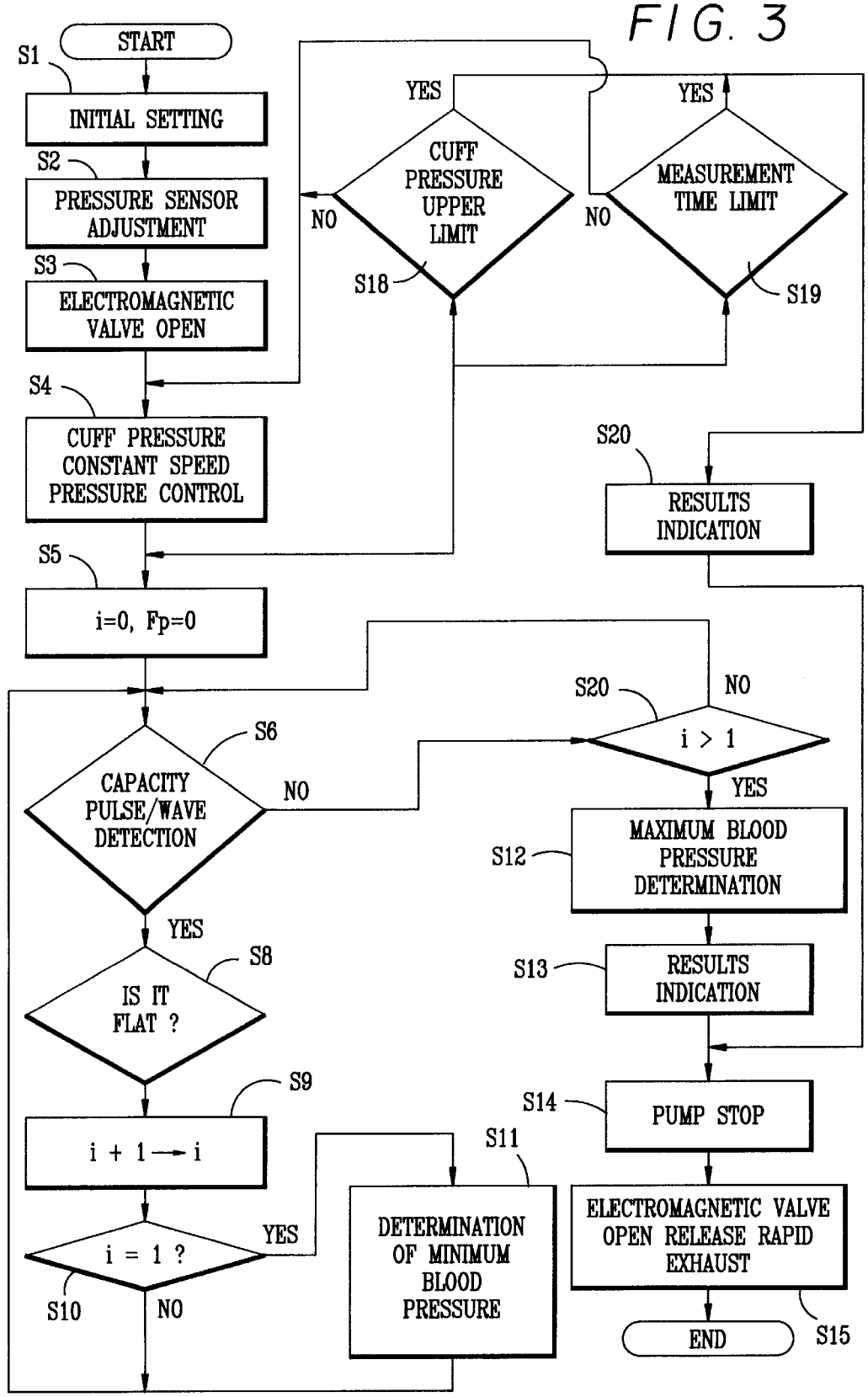
FIG. 3 is a flow chart showing one example of processing procedures when measuring the blood pressure by a sphygmomanometer shown in FIG. 1.

The digital data processing section 14 is composed of a so-called microcomputer, which includes a CPU and memory, And a display section 38 which is able to display the maximum blood pressure and minimum blood pressure is connected to this digital data processing section 14 via an interface. In FIG. 3 is shown one example of processing procedures in the blood pressure measurement which is carried out in this digital data processing section 14.

When measuring the blood pressure, a cuff 10 is attached to the upper arm 16 of a patient, so that a reflection plate 12b is positioned on the artery of the upper arm 16, and cloths 10b, 10c are fixed by applying the same onto the engaging fastener 10e.

Furthermore, in this case, in order to securely position the reflection plate 12b on the artery of the upper arm 16 of a patient, for example, as shown by hypothetical lines in FIG. 2, it is preferable that a plurality of optical range sensors 12 are disposed along the circumferential direction. With such a construction, a reflection plate 12b of any one of the sensors 12 is able to be positioned on the artery. In a case where a plurality of optical range sensors 12 are used, one which is outputting the largest output signals may be selected by comparing the output values of the respective sensors 12.

Upon a completion of attaching the cuff 10, since the preparation of measuring the blood pressure is then completed, the control procedure of the digital data processing section 14 is commenced, wherein firstly the initial setting is carried out in step s1. This initial setting includes the upper limit value of pressure given to the cuff 10 and the limit of the measuring time. After this initial setting is completed, a calibration of the pressure sensor 20 is performed in step s2, and an output signal is sent to the solenoid control section 22 in step s3 in order to open the solenoid control valve 22.

Next, in step s4, the solenoid control valve 22 is controlled on the basis of detection signals of the pressure sensor 20, wherein a constant speed compression control which increases the pressure inside the air bag 10d of the cuff 10 at a constant speed is performed.

At this time, with a cuff 10 according to this preferred embodiment, since reinforcing fibers 10f are incorporated in a bag member 10g of the air bag 10d in a latticed state and a hard curved plate 10a intervenes at the outer circumferential side of the bag member 10d, the elongation and contraction of the bag member 10d are regulated, and at the same time the expansion thereof outward of the bag member 10d is regulated by the curved plate 10a, whereby the optical range sensors 12 are able to be prevented from being displaced. Resultantly, it will be possible to exert pressure upon the artery with the outside position of the bag member 10d kept constant.

Continuously, in step s5, flag i which expresses the number of artery waves is set to zero (0), and at the same time the blood pressure judgement flag $F_P$ is also set to zero (0), whereby output signals of an optical range sensor 12 are taken in. In step s6, it is judged whether or not the photoelectric volumetric pulse wave signals are detected.

Figure 4:
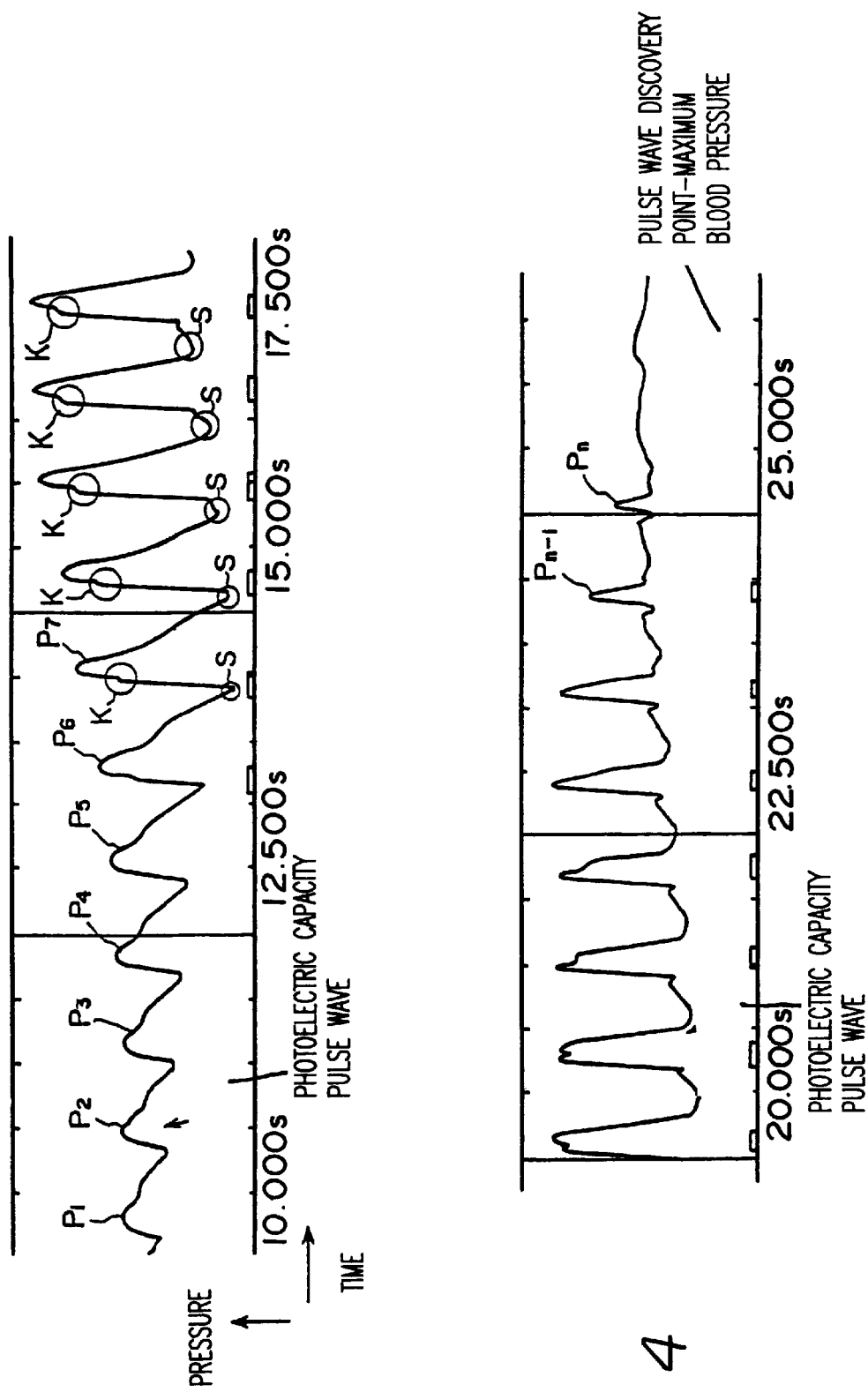
FIG. 4 is a pulse wave diagram showing one example of pulse waves detected by a sphygmomanometer shown in FIG. 1.

The photoelectric volumetric pulse wave signals judged herein are those shown in FIG. 4 and are those in which the part corresponding to the expansion of the air bag 10d which is compressed at a constant speed is eliminated from the output signals of the optical range sensor 12, and parts corresponding to the pulsation per pulse are individually extracted and stored into memory.

In step s6, in a case where no photoelectric volumetric pulse wave signal is detected, the process advances to step s7, wherein in a case where it is judged that the flag i is not larger than 1, the process is caused to return to step s6. In this case, if it is judged in the first process in step s6 that no volumetric pulse wave is detected, since the flag is set to zero (0) in step s5, the process is returned to step s6 without fail.

Accordingly, it is judged in step s6 that a photoelectric volumetric pulse wave signal has been detected, it is judged in step s8 whether or not a flat section exists in the photoelectric volumetric pulse wave signals equivalent to one pulse detected in step s8. If no flat section exists, the process returns to step s6, wherein the process similar thereto is repeated. On the other hand, if it is judged that a flat section exists in the photoelectric volumetric pulse wave signals, 1 is added to the flag i in step s9, whereby this is regarded as a new flag i and the process advances to step s10.

In step s10, it is judged whether or not the flag i is 1. If it is 1, the minimum blood pressure is judged in step s11. The process returns to step s6 in a case where the flag is not 1 in step s10 and when the judgement of the minimum blood pressure is finished in step s11.

The process till the above judgement of the minimum blood pressure is more concretely described below. For example, herein it is assumed that the photoelectric volumetric pulse wave signals P1, P2, P3, ... Pn per pulse are extracted in a state shown in FIG. 4. It is judged in step s8 whether or not any flat section exists in the respective photoelectric volumetric pulse wave signals P1, P2, P3, ... Pn detected in step s6.

Herein, in the process of increasing pressure in the air bag 10d at a constant speed, in a case where the pressure in the air bag 10d is lower than the minimum blood pressure of a patient, the photoelectric volumetric pulse wave signals pulsate without being influenced by the pressure of the air bag 10d (Photoelectric volumetric pulse wave signals P1 to P6 in FIG. 4).

However, if the pressure in the air bag 10d becomes larger than the minimum blood pressure of a patient, a flat section s having no pressure fluctuation in the photoelectric volumetric pulse wave signals when the artery pressure is smaller than the pressure in the air bag 10d. Accordingly, this preferred embodiment is constructed so that a photoelectric volumetric pulse wave signal at which a flat section s occurs for the first time in steps s8 to s10 is detected, and the minimum blood pressure is judged when this photoelectric volumetric pulse wave signal P7 is detected.

In the judgement of the minimum blood pressure in step s11, for example, the pressure in the air bag 10d at the moment when the photoelectric volumetric pulse wave signal p7 at which a flat section s occurs for the first time is extracted may be made the minimum blood pressure value, or the pressure in the air bag 10d at the moment when the photoelectric volumetric pulse wave signal P6 immediately before the photoelectric volumetric pulse wave signal p7 at which a flat section s occurs for the first time is extracted may be made the minimum blood pressure value, or the mean value of the pressure in the air bag 10d at the moment when the photoelectric volumetric pulse wave signal P7 and the photoelectric volumetric pulse wave signal P6 are extracted may be made the minimum blood pressure value.

Furthermore, in the judgement of the minimum blood pressure in this case, as shown in FIG. 4, since a high speed displacement portion K equivalent to Korotoff's sounds appears in the photoelectric volumetric pulse wave signals if the pressure in the air bag 10d becomes larger than the minimum blood pressure of a patient, the photoelectric volumetric pulse wave signal where this high speed displacement portion K occurs for the first time is detected in step s8, and the minimum blood pressure value may be obtained by the method already described in step s11. Furthermore, similarly, it is possible to obtain the minimum blood pressure value by detecting both the flat sections and the high speed displacement portion K.

As described above, the minimum blood pressure is judged. Even though a flat section s exists in the photoelectric volumetric pulse wave signal after the value is specified, it is not judged in step s10 that the flag i is 1. Therefore, the processing procedures in step s6 to step s10 are carried out one after another. And if it is judged in step s6 that no photoelectric volumetric pulse wave signal is detected, step s7 is executed again.

In the judgement in step s7 at this time, since the processing procedure from step s6 to step s1 is repeated several times, the flag i becomes larger than 1 without fail. Therefore, step s12 is consecutively executed, wherein the maximum blood pressure is judged.

That is, with a sphygmomanometer according to this preferred embodiment, if the pressure inside the air bag 10d becomes larger than the maximum blood pressure when increasing the same at a constant speed, the artery pulsation is suppressed by the pressure, whereby no displacement occurs in an optical range sensor 12. Taking note of this point, the point when no photoelectric volumetric pulse wave signal will be detected is judged as the maximum blood pressure of a patient.

When the maximum blood pressure is judged in step s12 and the value thereof is obtained, the result of measurement is displayed on the display section 38 in step s13. Consecutively, in step s14, after the pump 24 is caused to stop, the solenoid control valve 22 is made open to the atmosphere in step s15 to cause the air inside the air bag 10d to be rapidly exhausted. Here, the process ends.

On the other hand, in addition to the above procedures, as a constant speed compression of the air bag 10d is commenced in step s4, it is always judged in step s18 whether or not the pressure inside the air bag 10d is larger than the initially set upper limit value. Furthermore, simultaneously with the above judgement, it is judged in step s19 whether or not the measurement time is over. If it is judged that either of them exceeds the respective limits, the meaning thereof is displayed on the display section 38 in step s20, whereby the process is shifted to step s14, and the measurement is interrupted.

Since a sphygmomanometer constructed as described above has an optical range sensor 12 which is disposed opposite the air bag 10d of the cuff 10 and is able to detect the pulsation displacement of the artery can judge the maximum blood pressure and minimum blood pressure of a patient with its digital data processing section 14 on the basis of photoelectric volumetric pulse wave signals outputted from said optical range sensor 12, it is possible to directly measure the local displacement quantity of the artery wall and to obtain the maximum blood pressure and minimum blood pressure on the basis of this displacement quantity, whereby it is possible to accurately measure the blood pressure values.

Figure 5:
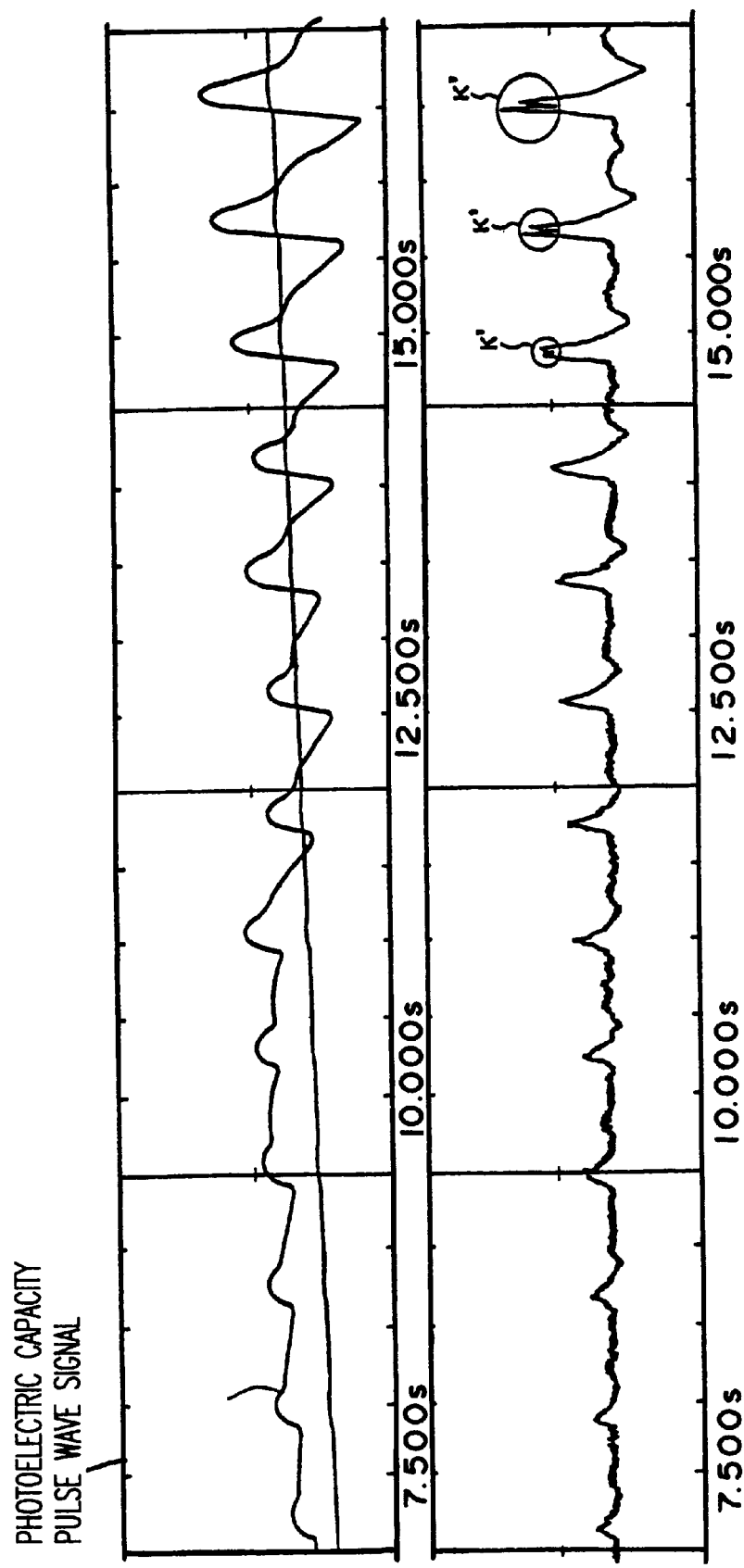
FIG. 5 is a pulse wave diagram showing another example when measuring the minimum blood pressure by a sphygmomanometer shown in FIG. 1.

FIG. 5 shows another example of judgement methods of the minimum blood pressure, which can be employed for a sphygmomanometer according to the invention. In the example shown in the same drawing, the photoelectric volumetric pulse wave signals obtained by the optical range sensor 12 are differentiated, and the minimum blood pressure can be judged with this differentiated photoelectric volumetric pulse wave signals. In the same drawing, the wave forms shown in the upper stage are photoelectric volumetric pulse wave signals and those shown in the lower stage are their differentiated wave forms.

If the photoelectric volumetric pulse wave signals obtained by the optical range sensor 12 are differentiated, the parts which are changing at a high speed, that the parts corresponding to Korotoff's sounds K' are intensified, and as shown at the right end in FIG. 5, they appear as a great change. Therefore, in this example, the part where Korotoff's sound appears for the first time, or the vicinity thereof is judged as the minimum blood pressure. According to such a judgement of the minimum blood pressure, since it is possible to accurately recognize the part corresponding to Korotoff's sounds K', it is possible to more accurately judge the minimum blood pressure.

Figure 6:
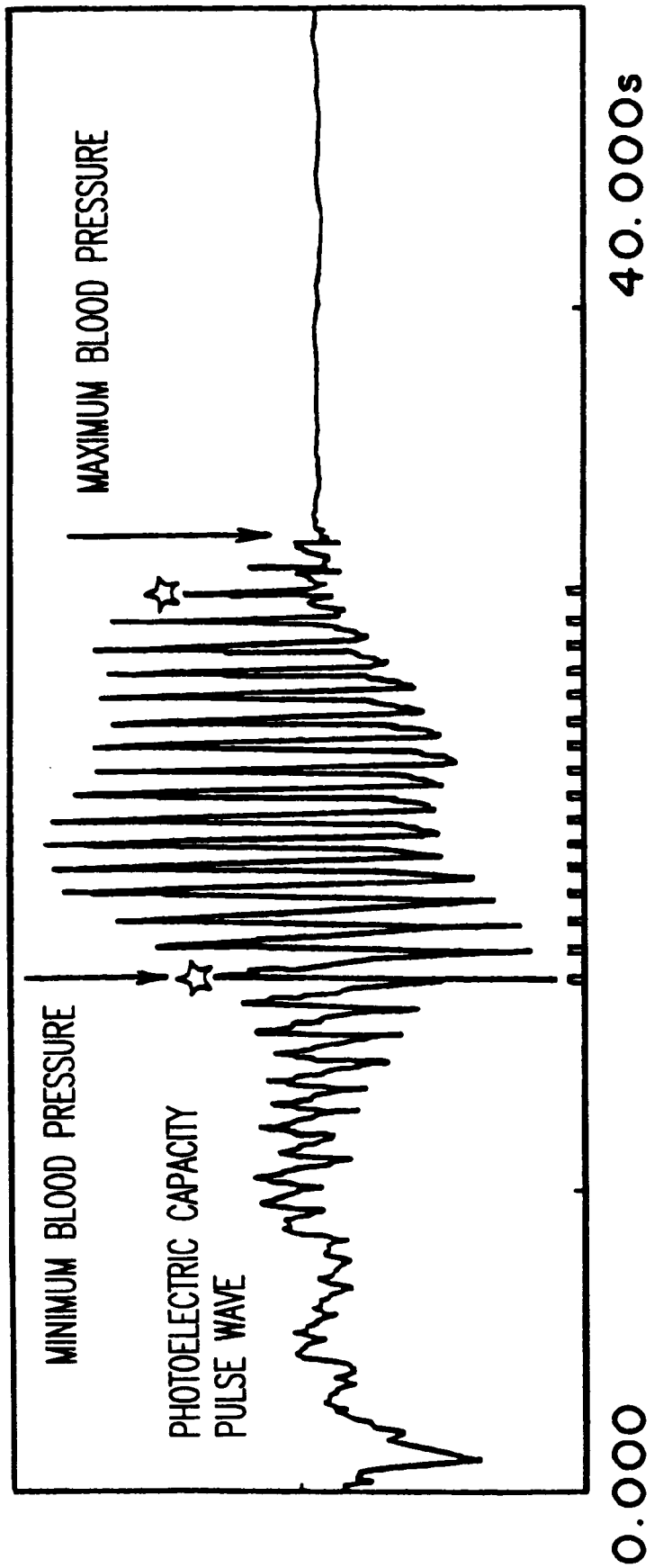
FIG. 6 is a pulse wave diagram showing still another example when measuring the minimum blood pressure by a sphygmomanometer shown in FIG. 1.
Figure 7:
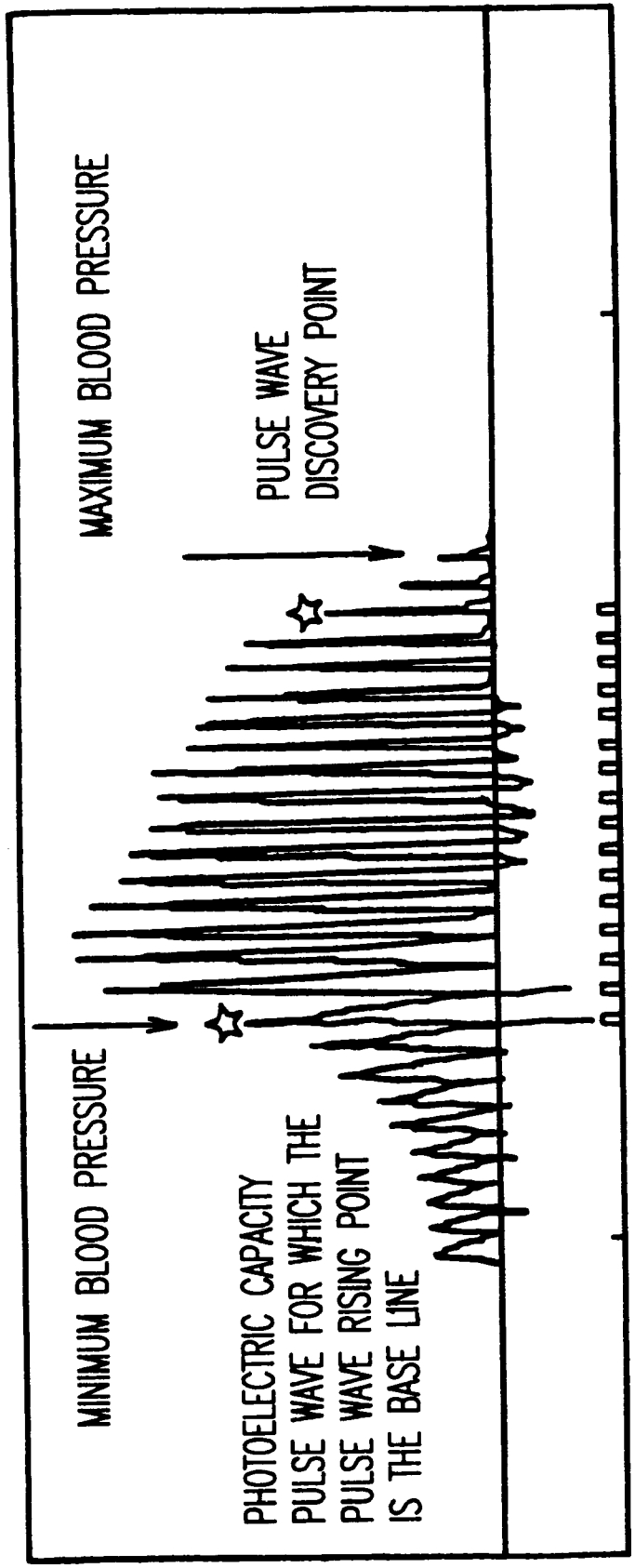
FIG. 7 is a pulse wave diagram showing further another example when measuring the minimum blood pressure by a sphygmomanometer shown in FIG. 1.

FIG. 6 and FIG. 7 show still another example of judgement methods of the minimum blood pressure, which can be employed for a sphygmomanometer according to the invention. In the example shown in FIG. 6, each peak value of the photoelectric volumetric pulse wave signals obtained by the optical range sensor 12 is obtained, the part at which the fluctuation ratio is largest in the comparison of the values before and after the peak value thus obtained is specified, whereby the rising of the photoelectric volumetric pulse wave signal being the peak value is judged as the minimum blood pressure.

In the example shown in FIG. 7, the amplitude of photoelectric volumetric pulse wave signals obtained by the optical range sensor 12 is obtained, and the part of the maximum amplitude is specified by comparing the obtained amplitude, whereby the rising of the photoelectric volumetric pulse wave signal having the maximum amplitude is judged as the minimum blood pressure. Such a judgement method of the minimum blood pressure is also employed in a conventional oscillometric method. However, with a sphygmomanometer of the invention, since a displacement quantity of a local artery wall is directly measured by an optical range sensor 12 and the maximum blood pressure and minimum blood pressure are obtained on the basis of this displacement quantity, it is possible to further increase the judgement accuracy of the minimum blood pressure.

Furthermore, in the above preferred embodiment, a case where the maximum blood pressure and minimum blood pressure are judged in the process of increasing the pressure of the air bag 10g of the cuff 10 at a constant speed is shown. However, the invention is not limited to this embodiment. The maximum blood pressure and minimum blood pressure may be judged in the process of reducing the pressure thereof at a constant speed, wherein for example, the point at which a photoelectric volumetric pulse wave occurs may be judged as the maximum blood pressure. Industrial feasibility As described in the above preferred embodiment, with a sphygmomanometer according to the invention, since the displacement quantity of a local artery wall is directly measured by an optical range sensor and the maximum and minimum blood pressure values are obtained on the basis of this displacement quantity, the invention is suitable for a closed type sphygmomanometer which is able to accurately obtain the maximum and minimum pressure values.

What is claimed is:

1. A sphygmomanometer comprising:
    an inflatable cuff which is attached to a selected portion of a patient for applying pressure to an artery when inflated;
    an optical range sensor which is located on opposite sides of said cuff for generating photoelectric volumetric pulse wave signals correlating to the pulsation displacement of said cuff caused by said artery;
    a digital processing means for determining a maximum and minimum blood pressure of said patient solely on the basis of said photoelectric volumetric pulse wave signals generated by said optical range sensor; and
    a display section for displaying the maximum and minimum blood pressure values determined by said digital data processing section, wherein when raising or lowering an inflation pressure inside the cuff at a constant speed, said digital data processing section determines said maximum blood pressure by determining a point of disappearance or appearance of said photoelectric volumetric pulse wave signals, and determines said minimum blood pressure by determining a point at which said photoelectric volumetric pulse wave signals rapidly decrease.

2. A sphygmomanometer as defined in claim 1, wherein when raising or lowering the pressure inside the cuff at a constant speed, said digital data processing means determines a point of disappearance or appearance of said photoelectric volumetric pulse wave signals as the maximum blood pressure, and determines a point at which Korotoff's sound constituents appear from said photoelectric volumetric pulse wave signals as the minimum blood pressure.

3. A sphygmomanometer as set forth in claim 1 or 2, wherein when raising or lowering the pressure inside the cuff at a constant speed, said digital data processing determines a point of disappearance or appearance of said photoelectric volumetric pulse wave signals as the maximum blood pressure, and determines a point, at which a vicinity of a flat section appears with respect to said photoelectric volumetric pulse wave signals as the minimum blood pressure.

4. A sphygmomanometer as set forth in claim 1, further including a plate for limiting the outer dimensions of the inflatable cuff.

* * * * *